United States Patent [19]

Holtkamp

[11] Plant 4,239

[45] Apr. 11, 1978

[54] AFRICAN VIOLET PLANT

[76] Inventor: Reinhold Holtkamp, Wertherstrasse 112, 4294 Isselburg, Germany

[21] Appl. No.: 786,852

[22] Filed: Apr. 12, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet which is a mutation of Colorado, disclosed in my pending application Ser. No. 764,216, filed Nov. 30, 1976. The mutation is characterized by its large white flowers having frilled edges, red-violet in certain areas, and by its vigorous growth, upright and strong flower stems and profuse flowering.

2 Drawing Figures

The present invention comprises a new and distinct cultivar of African violet plant, botanically known as *Saintpaulia ionantha,* and known by the cultivar name Nevada.

The new cultivar, identified during the breeding and selection process by the designation is a mutation of my cultivar Colorado, disclosed in my pending application Ser. No. 746,216, filed Nov. 30, 1976. Most of the characteristics of Nevada are the same as Colorado, except variations in leaf size, shape and color, and flower size and color. Colorado is characterized by its deep red flowers with frilled edges, whereas the mutation Nevada has white flowers with areas of red-violet in the frilled edges thereof.

The new cultivar Nevada was discovered and selected as a flowering plant in a block of plants of the parent cultivar. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Nevada which in combination distinguish this African violet as a new and distinct cultivar:

1. Large flowers with frilled edges, wherein the flowers do not drop.
2. White flowers with red-violet edges in certain areas.
3. Profuse flowering on strong stems, and a long blooming period.
4. Vigorous growth, and upright flower stems.
5. An attractive saleable plant is present at the first flash of flowers.
6. Compact growth habit.

The accompanying photographic drawings show a typical specimen plant of the new cultivar.

FIG. 1 shows a finished plant and

FIG. 2 illustrates various components of the plant, top side and underside, at various stages of growth. The colors appearing in the photographs are as true as possible with color illustrations of this type.

In the following description, color references are made to The Munsell Limit Color Cascade, 1972 edition, except where general color terms of ordinary significance are obvious.

Botanical classification: *Saintpaulia ionantha,* Ramat. cv. Nevada.

Parentage: Mutation out of Colorado.

Propagation: The new cultivar holds its distinguishing characteristics through successive propagations by leaf cuttings and by division of shoots.

Plant: From 7 to 10 cm. tall when grown in pots, and approximately 25 cm. in diameter when fully grown.

*Leaves.*—General Form: Oval. Diameter: 45-65 mm. Texture: Soft, hairy. Aspect: Velvety. Veins: Underside, well pronounced. Color (upperside): 21-15. Color (underside): 20-1. Petiole: Light green, approximately 23-2.

Flowers:

*Buds.*—Ball-shaped, approximately 8–10 mm.; before opening, color 21-2.

*Sepals.*—Five, same size. Color: 21-3 on the base. Calyx: Funnel-shaped. Aspect: Spear-shaped, tips turning in color to brownish. Peduncle: 21-3, strong, upright, 2-3 cm.

Individual flowers:

*Size.*—40-50 mm., almost flat.

*Color.*—Upperside: white, shiny, with violet-red edges in certain areas; underside: white, with violet pattern.

*Borne.*—Most flower stems have 50-10, and frequently more flowers.

*Shape.*—Five; two small, three large, all having frilled edges.

*Corolla.*—The large petals are 25 to 27 mm. long measured from the center of the flower. A few petals have clean white edges while others have red-violet edges.

*Arrangement.*—Strong upright peduncles with up to 10 and more flowers.

*Flowering time.*—Approximately 6–8 weeks after potting the first flower appears, and three weeks thereafter the plant is in full flower.

Reproductive organs:

*Stamens.*—Two, 4 mm., color golden yellow; seed capsule pushes slightly through.

*Anthers.*—27-4.

*Arrangement.*—Basifixed.

*Filaments.*—Green yellow, color 26-3.

*Styles.*—Upper part light violet color, 46-7: base light green, hairy.

*Pollen color.*—26-2.

Roots: Well developed root system; roots are white when young and active.

Disease resistance: Good as experienced to date.

General observations: Nevada is a unique cultivar and provides for the first time an African violet having white flowers with frilled petal edges, some areas of which are red-violet in color. The flowers are carried on strong, upright stems, and the flower color does not fade on maturity, nor do the petals drop. The flowering is profuse and the blooming period relatively long, and although Nevada does not continuously bloom, there are second and further blooming periods at approximately 7–8 week intervals, and the subsequent flowerings are even more attractive than the original flowering, with the flowers being relatively larger in diameter and the stems relatively stronger.

I claim:

1. A new and distinct cultivar of African violet known by the cultivar name Nevada and characterized particularly as to uniqueness by the combined characteristics of large, white flowers having frilled edges, with certain areas of the edges being red-violet in color; vigorous growth; strong, upright flower stems, and profuse flowering; compact growth habit, and by the plant being saleable at the first flash of flowers.

* * * * *

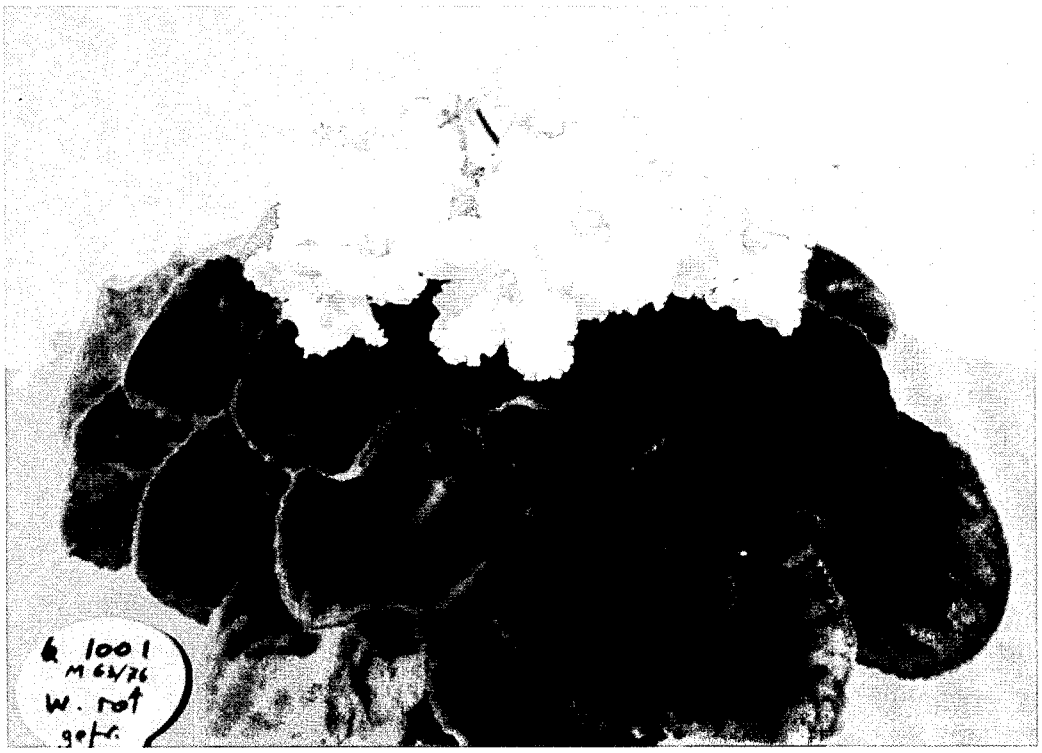
1001
M 6/76
W. rot

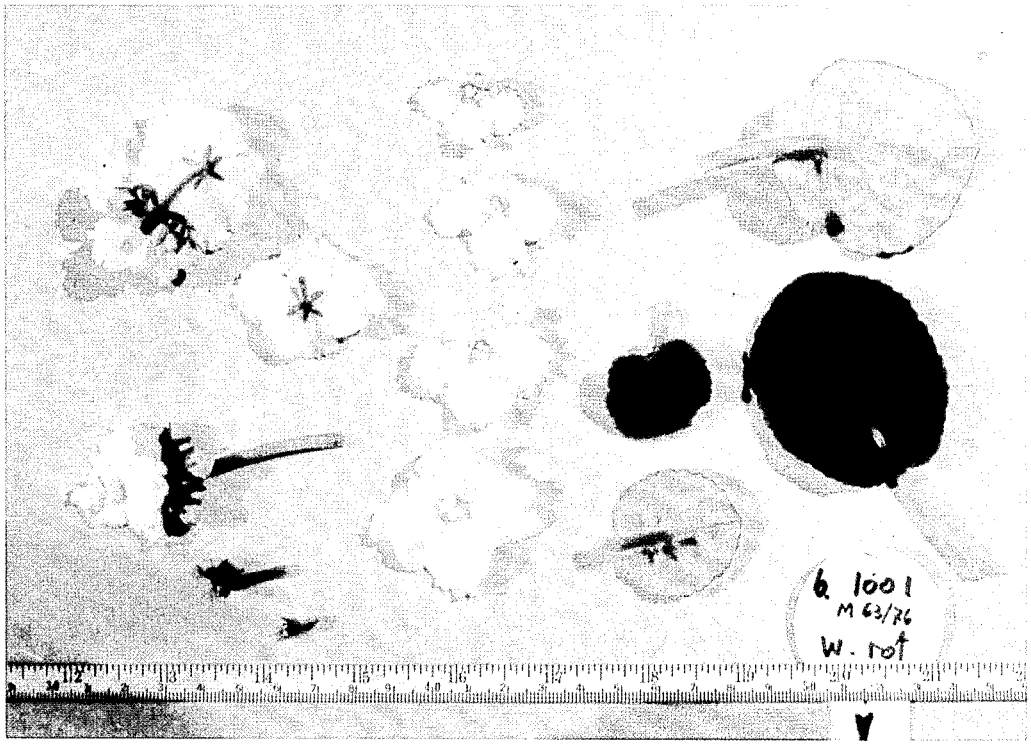
6 1001
M 63/76
W. rot